United States Patent [19]

Fehder

[11] Patent Number: 5,166,075
[45] Date of Patent: Nov. 24, 1992

[54] METHOD FOR DETERMINING WHETHER RESPIRATORY GAS IS PRESENT IN A GASEOUS SAMPLE

[75] Inventor: Carl G. Fehder, Cherry Hill, N.J.

[73] Assignee: Nellcor Incorporated, Hayward, Calif.

[21] Appl. No.: 873,971

[22] Filed: Apr. 24, 1992

Related U.S. Application Data

[60] Continuation of Ser. No. 136,600, Dec. 22, 1987, abandoned, which is a division of Ser. No. 896,360, Aug. 13, 1986, Pat. No. 4,728,499.

[51] Int. Cl.[5] .................... G01N 31/22; G01N 33/497
[52] U.S. Cl. .................... 436/133; 128/719; 422/56; 422/57; 422/58; 422/87; 436/163; 436/166; 436/167; 436/169
[58] Field of Search .................... 422/56–58, 422/87; 436/133, 163, 166, 167, 169; 128/719

[56] References Cited

U.S. PATENT DOCUMENTS

| | | | |
|---|---|---|---|
| 2,136,236 | 11/1938 | Draper | 436/133 X |
| 3,373,735 | 3/1968 | Gallagher | 422/58 X |
| 3,467,601 | 9/1969 | Brauer | |
| 3,505,022 | 4/1970 | Luckey | 436/133 X |
| 3,694,164 | 9/1972 | Guenther | |
| 3,830,630 | 8/1974 | Kiefer et al. | 436/133 X |
| 4,144,306 | 3/1979 | Figueras | 422/56 |
| 4,691,701 | 9/1987 | Williams | 128/207.14 |
| 4,790,327 | 12/1988 | Despotis | 422/85 X |
| 4,879,999 | 11/1989 | Leiman et al. | 128/207.14 |

FOREIGN PATENT DOCUMENTS

| | | |
|---|---|---|
| 592882 | 2/1960 | Canada .................... 436/133 |
| 1007525 | 8/1955 | Fed. Rep. of Germany . |
| 1043988 | 9/1966 | United Kingdom . |

OTHER PUBLICATIONS

Anesthesiology, 60:613–614, 1984–The Einstein Carbon Dioxide Detector, J. A. Berman, Joseph J. Furgiuele, G. F. Marx.

*Primary Examiner*—Jill A. Johnston
*Attorney, Agent, or Firm*—Cooper & Dunham

[57] ABSTRACT

A method is disclosed for determining whether respiratory gas is present in a gaseous sample by which the sample is brought into contact with an indicator which yields an indication within a diagnostically effective period of time of the presence in the sample of carbon dioxide in concentration of at least 2% while an indication of the presence of carbon dioxide in a sample of ambient air would be delayed beyond a predetermined period of time. The method has particular utility in determining the correct placement of an endotracheal catheter in a patient or in the detection of apnea.

25 Claims, 2 Drawing Sheets

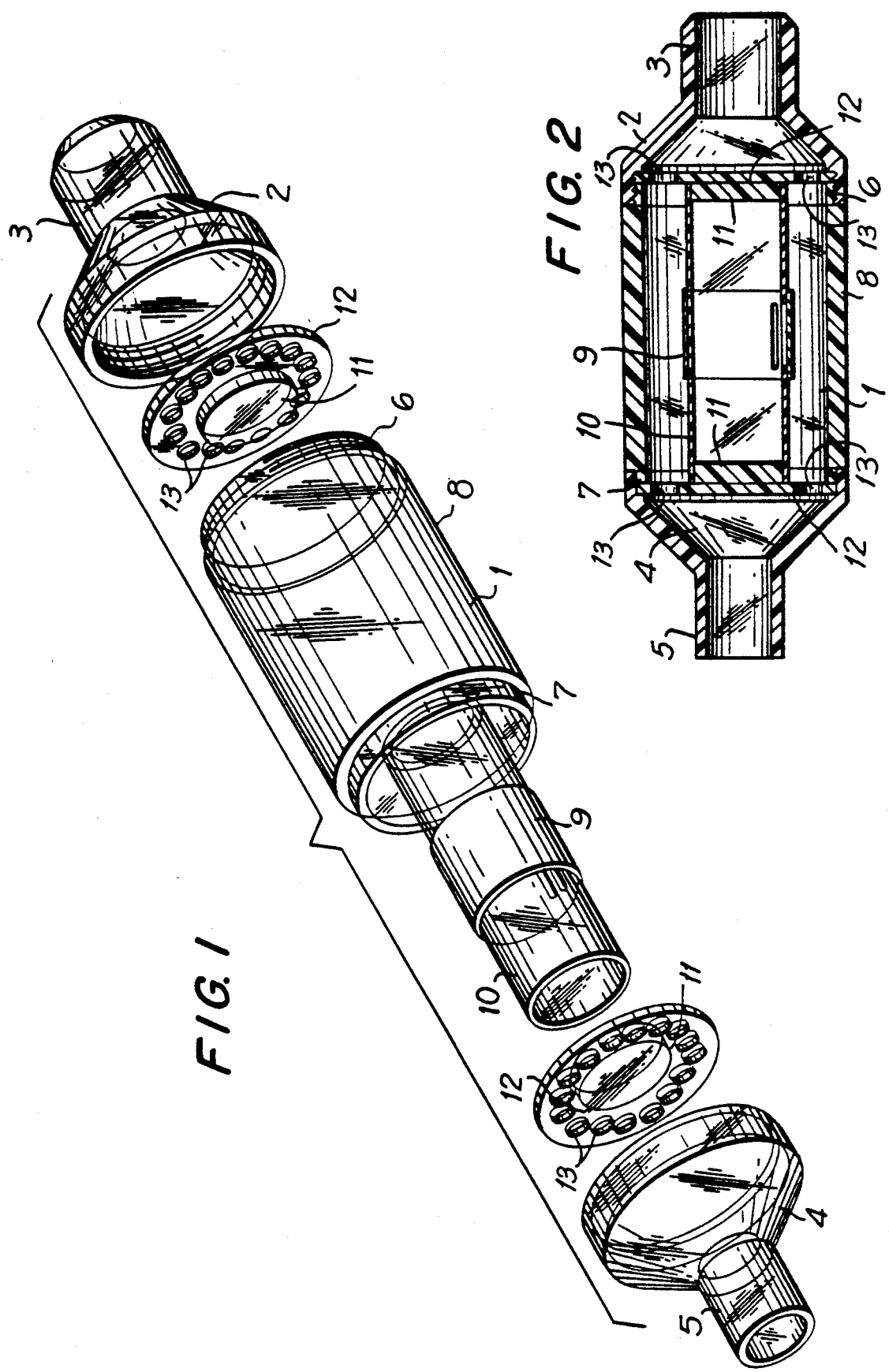

METHOD FOR DETERMINING WHETHER RESPIRATORY GAS IS PRESENT IN A GASEOUS SAMPLE

This is a continuation of application Ser. No. 136,600, filed Dec. 22, 1987, now abandoned, which in turn is a divisional of application Ser. No. 06/896,360, filed Aug. 13, 1986, now U.S. Pat. No. 4,728,499.

BACKGROUND OF THE INVENTION

This invention relates to an indicator device, more particularly a rapid response device for the detection of carbon dioxide in a gas mixture. The invention is also concerned with a method for determining the correct placement of an endotracheal catheter in the trachea of a patient, particularly during apnea, by use of such indicator device.

Devices for the detection of carbon dioxide which rely in part upon the change in color of certain chemical compounds according to the pH of their environment are known in the art. Such chemical indicators change color in solution when the pH of the solution changes.

Numerous examples of chemical indicators which are pH-sensitive, and thereby useful in carbon dioxide indicator systems, have been disclosed in the prior art.

U.S. Pat. No. 2,890,177 discloses a liquid chemical indicator for detecting the presence of carbon dioxide in respiratory gases comprising an aqueous solution of an alkali metal oxalate and a pH sensitive dye which changes color at a pH in the range of 6.6 to 5.8.

U.S. Pat. No. 3,068,073 discloses a method of determining carbon dioxide in a gas which comprises passing the gas to be tested through a solid reagent comprising activated alumina carrying thymol blue and, optionally, a base.

U.S. Pat. No. 3,114,610 discloses a continuous sampling gas analyzer comprising a pH sensitive dye suspended in a gel substance, a semi-permeable membrane which separates the gas to be tested from the dye but allows gas to pass therebetween for analysis, a light source for illuminating the dye and a detector for analyzing the light transmitted through said dye. For carbon dioxide determination the dyes disclosed are Methyl Red and Bromcresol Green.

U.S. Pat. No. 3,754,867 discloses a gas analyzer which uses a light source to transmit light through a multi-layered sensor unit and a detector to receive and analyze the color change of a pH-sensitive indicator in one of said layers, said color change being a function of the concentration of carbon dioxide in the gas being measured. Examples of acid base indicators disclosed are phenol red, brilliant yellow, meta-cresol purple, cresol red, neutral red, m-nitrophenol and m-dinitrobenzoylene urea.

The various devices and compositions disclosed in the above-mentioned prior art references provide means for detecting or indicating the presence of carbon dioxide under certain circumstances. However, none of the said references directly addresses the problem of determining accurately and rapidly the correct positioning of an endotracheal catheter in the trachea of an apneic patient.

Introduction of a catheter in the trachea of a human may be required for a number of reasons. For example, in a hospital, an endotracheal catheter, also known as an intratracheal catheter, may be used for general anesthesia; in the field, a doctor or para-medic may use an endotracheal catheter to resuscitate an apneic patient. In both of these instances, and others, it is critical that the catheter be properly placed in the trachea and not, for example, in the esophagus. If the catheter is improperly placed and the error is not discovered within a diagnostically effective time, of the order of 5 to 20 seconds for example, the patient may begin to suffer irreparable harm or even death.

In view of the criticality of the timing when an endotracheal catheter is improperly placed in an apneic patient, there is clearly a need for a simple device which will rapidly and reliably given an indication of improper (or proper) placement. (See P.K. Birmingham et al. "Esophageal Intubation", *ANESTH ANALC,* 1986, 65, 886-91).

A device for simplifying, expediting and making safe the technique of introduction of an intratracheal catheter is disclosed in U.S. Pat. No. 2,638,096. This device uses a perforate whistle which is adapted to sound an audible signal, and thus given evidence of even feeble breathing, when the catheter is properly placed in the trachea. However, the device is designed for the administration of general anesthesia to a patient with spontaneous respiration and the absence of an audible signal, for example when treating an apenic patient, does not necessarily mean that the catheter has been improperly placed.

It is known that the concentration of carbon dioxide in the atmosphere is normally about 0.03%, whereas the concentration of carbon dioxide in the gas exhaled by a human being is normally 4.5 to 5.0%. The normal amount of carbon dioxide in the esophagus of a human being is negligible. Accordingly it is evident that a rapid, accurate determination of the presence (or absence) of carbon dioxide in the gas exhaled by a human being will provide a clear indication as to whether the tube carrying said gas is properly placed in the trachea or improperly placed in the esophagus.

An apparatus for indicating the presence and relative amounts of carbon dioxide in gases breathed by patients is disclosed in U.S. Pat. No. 2,136,236. However, this apparatus utilizes a liquid solution for detection and it is concerned with the determination of gases in a closed breathing circuit, such as an oxygen tent.

It has now been found that the correct placement of an endotracheal catheter can be determined simply and rapidly by attaching to the distal end of said catheter a device embodying a rapid response carbon dioxide indicator.

SUMMARY OF THE INVENTION

In accordance with the invention described and claimed in the patent U.S. Pat. No. 4,728,499 there is provided a method for detecting the presence of approximately 2% carbon dioxide in a gaseous sample within a diagnostically effective period of time while delaying indications of the presence of carbon dioxide upon exposure to ambient air A combination rapid response device may be used for the detection of carbon dioxide in a gas mixture which comprises an enclosure defined by walls and having a transparent window in one of said walls an inlet, an outlet and atmospheric sealing means said enclosure having mounted therein an indicator component positioned and arranged to be viewed through so as said transparent window, said component comprising in a preferred embodiment a carrier having fixedly attached thereto an indicating element formed from (1) an aqueous solution of a colorless compound, i.e. base, which provides an alkaline solution; (2) a hygroscopic, high boiling, transparent, colorless, water-miscible liquid; and (3) a chromogenic pH-sensitive indicator which changes color relative to a change in pH of the solution and which has a PK which is preferably lower by 1.0-1.5 pH units than the pH of the solution; wherein the nature and concentration of the colorless compound in (1) is correlated to the nature and concentration of indicator (3) so that no color change occurs within a predetermined period of time which may be selected to be at least 15 minutes when the indicating element is exposed to an atmosphere having a concentration of 0.03% carbon dioxide, but a color change is produced within a diagnostically effective period of time which may be less than about 20 seconds, as desired, when said indicating element is exposed to an atmosphere containing at least 2% carbon dioxide. and sealing means which may be constructed so as to protect the indicator component from ambient air prior to use and is to be opened immediately prior to use of the device.

The carrier of the indicating element may be any solid material having no inherent acid or basic properties an dto which said indicating element may be fixedly attached either by impregnation or as a coating. As used herein the term "fixedly attached" means that the indicating element is not only impregnated or coated on to the carrier but also that the final reagent solution, from which the indicating element is formed, is incapable of flowing or migrating from the carrier while the device is in use. If necessary, the indicating element is suitable immobilized, for example, by drying to remove excess moisture.

Since the color change providing the required carbon dioxide determination is essentially a surface phenomenon, it is necessary that the carrier provides an appropriate surface area for the indicating layer. Equally important, the carrier should be made from a material which will not produce dust or fumes as these may expose the patient to potentially dangerous conditions.

Accordingly, a particularly preferred carrier is a thin layer of bibulous material, such as filter paper or fibrous synthetic material, and the indicating component is formed by impregnating said bibulous material with said indicating element and drying to remove excess moisture. Other materials which may be used as the carrier include plastic beads and inorganic crystals.

In accordance with the present invention there is provided in its preferred embodiment a method for determining the correct placement of an endotracheal catheter in the trachea of a patient which comprises connecting to the distal end of an endotracheal catheter, after introducing said catheter in a patient, preferably through the patient's mouth, and presumably into the patient's trachea, and inflating the sealing cuff, a combination rapid response device for the detection of carbon dioxide in a gas mixture which comprises an enclosure having a transparent window, an inlet and an outlet. The device includes an indicator component positioned and arranged within the enclosure so as to be viewed through the transparent window. The indicator component is preferably composed from a suitable carrier on which has been deposited an aqueous solution of a colorless alkaline compound, a hygroscopic, high boiling, transparent, colorless, water-miscible liquid and a chromogenic pH-sensitive indicator responsive to a change in pH of the solution. The preferred responsive indication is such that no color change occurs for 15 minutes in the presence of ambient air but a color change is produced preferably within 5 to 20 seconds in the presence of gas containing at least 2% carbon dioxide, and then visually examining the indicator within said device, after several artificial positive pressure breaths, to ascertain whether a color change thereof indicates correct placement of said catheter within the patient's trachea by detection of the presence or absence of a concentration of at least 2% carbon dioxide in the exhaled breath. The preferred period of time for response of the device to at least 2% carbon dioxide set forth above may be adjusted so as to fall within such diagnostically effective time periods as may be desired and the response of the device to ambient air may be delayed beyond a predetermined period of time.

DETAILED DESCRIPTION OF THE INVENTION

The invention will be more particularly described with reference to a preferred embodiment which provides a convenient and comparatively simple device for obtaining a rapid and substantially fool-proof indication of the proper or improper placement of an endotracheal catheter in the trachea of a patient, particularly an apneic patient.

To achieve the desired objective the device includes an indicator element which responds positively and rapidly to the presence of a certain concentration of carbon dioxide, i.e. the amount of carbon dioxide which is present in the exhaled breath of a human being. This concentration is normally of the order of 4.5-5.0%, but possibly may be as low at 2%.

However, although an extremely rapid response, of the order to 5 to 20 seconds, is crucial for the successful operation of the device, it is equally important the the indicator should not be so sensitive that it changes color too quickly when exposed to an atmosphere containing some minimal amount of carbon dioxide, for example, ambient air which normally contains about 0.03% carbon dioxide, which minimal amount is substantially less than that present in exhaled breath.

Accordingly, the indicator used in the device according to the invention should have a pK which is lower by 1.0-1.5 pH units than the pH of the final solution within which it is dissolved. This means that the indicator will not change color instantaneously upon exposure to an atmosphere which contains a certain minimum amount of carbon dioxide, for example, ambient air, and the resultant delay will provide the operator with ample time to open the seal and connect the device to an endotracheal catheter after having placed the catheter in the patient's throat and having inflated the sealing cuff on the catheter.

It is to be understood that the exposed indicator may eventually change color upon continued exposure to ambient air, or any atmosphere containing minimal amounts of carbon dioxide, since even a slow rate of diffusion of carbon dioxide into the indicator zone will lead, in time, to a sufficient depletion of base to cause a color change.

The hydroxyl ions or amine residues present in the alkaline solution from which the indicating element of the device is formed react chemically with carbon dioxide to produce a carbonate and/or bicarbonate or carbamate moiety, respectively, as represented by the following equations:

(i) $CO_2 + 2H^- \rightarrow CO_3^- + H_2O$ (ii) $CO_3 + CO_2 + H_2O \rightarrow 2HCO_3^-$ (iii) $CO_2 + 2R_2NH \rightarrow R_2NCOO^- + R_2NH_2+$ This reaction depletes the hydroxyl ion or amine at the interface and thus lowers the pH of the surface of the indicating component. The depletion is opposed by diffusion of new base into the surface, a replenishment process which tends to maintain the pH in the surface equal to the bulk solution in the carrier.

This is a dynamic process, constantly changing with time and the balance at any given time depends upon the following theoretical scheme:

(1) the concentration of $OH^-$ or amine in the bulk of the solution impregnated in or coated on the carrier. This determines the rate of diffusion into the surface of the indicating element which, for this purpose, may be considered as a "reaction zone";

(2) the rate of the chemical reaction, determined by the nature of each specific reacting species.

This rate R may be expressed by the equation $$R = K_A[CO_2][A]$$

where: [] represents the concentration of the species in mole/liter.

$K_A$ is a constant, specific for the reactant species A;

(3) the contact time between the surface of the indicating component and the gas to which it is exposed;

(4) the composition of the specific bibulous carrier which will determine the diffusivity constant for A in the carrier and therefore the rate of diffusion of A into the reaction zone; and (5) the concentration of carbon dioxide int he gas. This determines the rate of diffusion of carbon dioxide into said reaction zone.

Items (1), (2), (3) and (4) will be predetermined by the manner in which the device is constructed and the manner in which it is used in practice. Thus, in the medial application discussed above, the contact time is predetermined to correspond with the time the indicator will change color rapidly when subjected to artificial positive pressure exhaled breath, e.g. 5 to 10 seconds. Only item (5), the concentration of carbon dioxide, is the variable parameter in the scheme.

For the particular device of the invention, items (1) and (2) are preferably selected such that the pH in the reaction zone decreases sufficiently to cause a color change in the indicator only if the concentration of carbon dioxide is greater than 2.0% for an exposure time of 5 to 20 seconds. For the proposed embodiment the concentration of $OH^-$ necessary for these kinetic performance characteristics will produce a pH of $9.6 \pm 0.2$ in the final indicator element solution which is impregnated into Whatman No. 1 filter paper.

As stated above, if the contact time is substantially prolonged, a color change may occur eventually upon exposure to air, i.e. when the carbon dioxide concentration is only 0.03%. Thus, it has been found desirable that prior to use the device be sealed under an atmosphere devoid of carbon dioxide, preferably by being packaged in a gas-impermeable metallic foil, until just before it is required for us.

Although a color change may occur eventually upon prolonged contact with ambient air, when the sealed package is opened it is desirable that no color change takes place for at least fifteen minutes. While this could be arranged by increasing item (1) while keeping all other parameters constant, such a change would alter the entire kinetics of the reaction and a color change would not occur within 5 to 20 seconds at a minimum 2% carbon dioxide level. Thus, the initial pH would be too high and the device would be out of calibration for its intended use.

Accordingly, to overcome the problem of providing a suitable delayed reaction in ambient air and yet a rapid response when desired, the preferred embodiment of the present invention uses an indicator with a pK value sufficiently lower than the pH of the solution, so that a color change does not occur upon fifteen minutes of exposure to ambient air. Under such exposure, the pH in the reaction zone will be decreasing, but too slowly to cause a color change in the indicator in the stated contact time.

Since none of the items (1), (2), (3) or (4) have been altered, the preferred embodiment according to the invention will behave in the desired manner when exposed for 5 to 20 seconds to a gas mixture containing a minimum of 2% carbon dioxide. Thus the device is still in calibration for its intended use.

It is to be understood that a change in any one of the parameters of the scheme will necessitate a change in the others if the performance characteristics of the device are to remain unchanged.

Thus, it is to be noted that the selection of the indicator will also affect the choice of base to provide the alkaline solution. If the pK of the indicator is low for the reasons stated above, it is possible, with certain bases, that the ph of the indicating element will not drop low enough to cause a color change, even in the presence of a 5% concentration of carbon dioxide.

For example, with sodium hydroxide the carbonate reaction product is water soluble and a base itself. This tends to buffer the decrease in pH and the latter may never reach the transition pH for an indicator of low pK.

Consequently, the choice of compound which provides an alkaline solution has to be correlated with the selection of pH-sensitive indicator.

Calcium hydroxide provides a particularly suitable source of hydroxyl ions for use in a device according to the invention. This compound is soluble enough in water to provide an appropriate concentration of hydroxyl ions in item (1) to calibrate the device for medical use, but its carbonate reaction product with carbon dioxide is insoluble and therefore unable to buffer the decrease in pH. This makes possible the use of an indicator with a lower pK, such as metacresol purple, rather than, for example, thymol blue or phenol phthalein. This is turn allows for a longer exposure time in air.

While barium hydroxide has a similar chemical profile to calcium hydroxide, because of its toxicity, it cannot be used in a medical device unless very strict precautions are taken to avoid any possible contact with the patient and user. Since an object of the present invention is to provide a device which is not only simple to use but also relatively cheap to produce, a device utilizing a potentially toxic material is impracticable. Furthermore, disposal of such material is subject to strict government regulatory guidelines.

Examples of suitable colorless compounds which provide an alkaline solution and which may be used in the device according to the invention, subject to the selection of accompanying indicator, are calcium hydroxide, sodium carbonate, lithium hydroxide, sodium hydroxide, potassium hydroxide, magnesium hydroxide, potassium carbonate, sodium barbital, tribasic sodium phosphate, dibasic sodium phosphate, potassium acetate, monoethanolamine, diethanolamine and piperidine.

As indicated above, calcium hydroxide is particularly preferred.

Examples of suitable pH-sensitive indicators for use in the device of the invention are metacresol purple, thymol blue, cresol red, phenol red, xylenol blue, a 3:1 mixture of cresol red and thymol blue, bromthymol blue, neutral red, phenolphthalein, rosolic acid, α-naphthelphthalein and orange I. Metacresol purple is particularly preferred and a particularly preferred combination of carrier, base and indicator is Whatman No. 1 filter paper, calcium hydroxide and metacresol purple.

By using a different carrier, for example Whatman No. 3, all the other parameters must be adjusted to maintain the same kinetic performance characteristics. Whatman No. 3 has a lower diffusivity constant for $OH^-$ than Whatman No. 1. Therefore, the concentration of $OH^-$ must be higher in the final solution producing a higher pH in the indicating component. This in turn, requires the selection of a matching pH indicator having a correspondingly higher pK, for example thymol blue.

A 3:1 mixture of thymol blue and cresol red has a pK very similar to metacresol purple and also may be used in a device according to the invention. However, this mixture adds complexity and the orange tinted yellow color achieved upon transition is not aesthetically pleasing.

Cresol red along has a pK even lower than metacresol purple, but the red to yellow transition is less visually dramatic than the purple to yellow of metacresol purple.

The other ingredient of the aqueous solution which forms the indicating element of the invention is a hygroscopic, high-boiling, transparent, colorless, water-miscible liquid. The purpose of this ingredient is to entrap sufficient water in the indicating element, for example when it is absorbed in a bibulous material and then dried in a hot air stream, to enable the exposed surface of the element to act as a reaction zone with the surrounding gas.

An essential criterion of the device is that the indicating element be immobilized in or on the carrier. This requires active drying of the impregnated carrier to achieve minimal moisture retention so as to prevent migration or flow of material while in use. However, since carbon dioxide will not react with the base without water, the presence of a certain minimum amount of water is necessary for the device to work. The hygroscopic liquid ensures that the required minimum amount of water is present in the indicating element when exposed to humid air or exhaled breath.

Examples of suitable hygroscopic liquids for use in the device of the invention are glycerol, propylene glycol, monoethylene glycol, diethylene glycol, polyethylene glycol and various aliphatic alcohols. Because they are non-toxic and have antiseptic properties which inhibit bacterial and fungal growth, glycerol and propylene glycol or mixtures thereof are particularly preferred.

The following Examples illustrate the preparation of the indicating element used in the device according to the invention.

EXAMPLE 1

A 0.003 M aqueous solution of calcium hydroxide was prepared by dissolving calcium hydroxide in 5 ml. of freshly boiled, distilled water. The pH of the resulting solution was 11.6 to 11.7. Metacresol purple sodium salt was added to the solution so that the concentration of the indicator was 0.12%. An equal volume of propylene glycol was added and the solution stirred to obtain a homogeneous mixture. A 10% additional volume of glycerol was added to the mixture. The glycerol improves pentrability and diffusion into the filter paper.

The resulting solution, having a pH of about 9.6, was applied to a double layer of Whatman No. 1 filter paper and the surface of the paper was then dried by passing a stream of heated air over it for several seconds.

The impregnated paper may be cut into strips and immediately used in a device according to the invention, as described hereinafter, or, if stored for future use, should be protected from prolonged exposure to ambient atmosphere by being stored in a sealed container under an atmosphere of nitrogen or over soda-lime granules.

When the impregnated strip is incorporated in a device according to the invention, said device is packaged in a gas impermeable metallic foil. Said package is sealed after the atmosphere therein has been purged from carbon dioxide by nitrogen gas or by air which has been passed over soda-lime granules.

The impregnated strip made in accordance with this Example stays purple for more than two hours in an atmosphere containing 0.03% carbon dioxide. Upon exposure to an atmosphere containing 5% carbon dioxide, the strip turns bright yellow within three to five seconds. In 2% carbon dioxide the yellow color is achieved in 7 to 10 seconds.

EXAMPLE 2

(a) A 0.0065 M aqueous solution of sodium carbonate was prepared by dissolving sodium carbonate in 5 ml. of carbon dioxide-free, distilled water. The pH of the resulting solution was approximately 11.0. 0.005% w/v of thymol blue was added to the solution. An equal volume of glycerol was added and the solution stirred to provide a homogeneous mixture having a pH of about 9.4.

The resultant mixture was absorbed on a strip of Whatman No. 1 filter paper and the impregnated paper was dried in a stream of hot air.

When exposed to varying concentrations of carbon dioxide, the impregnated strip responded as follows:

| $CO_2$ Concentration | Contact Time | Color of Strip |
| --- | --- | --- |
| 0 | ∞ | blue |
| 0.03% (ambient air) | 10 minutes | blue-green |
| 0.03% | 15 minutes | green |
| 2.0% | 5 seconds | yellow |
| 5.0% | 1 second | yellow |

This chemical system is slightly too sensitive, since some color change occurs in ambient air within 15 minutes.

(b) Example 2(a) above was repeated except that propylene glycol was substituted for the glycerol. The performance characteristics of the impregnated strip were substantially similar to those of the strip of (a) above.

EXAMPLE 3

A solution of sodium carbonate, water and glycerol was made up as in Example 2(a) but instead of thymol blue, the indicator was metacresol purple (sodium sat). Metacresol purple has a lower pK than thymol blue. The substitution of metacresol purple solves the sensitivity problem in ambient air but produces a very slight greenish that to the yellow color after 5 seconds expose to 5% carbon dioxide. This slightly incomplete transition is the result of buffering by the bicarbonate reaction product.

An interesting property of this system is its extremely rapid return to the original purple color when returned to ambient air. Accordingly, the pH 9.4, sodium carbonate, glycerol, metacresol purple indicator system is a useful alternative to the preferred calcium hydroxide system illustrated in Example 1.

The response characteristics of a strip of Whatman No. 1 filter paper impregnated with the solution of this Example are as follows:

| $CO_2$ Concentration | Contact Time | Color of Strip |
| --- | --- | --- |
| 0 | ∞ | bright purple |
| 0.3% | 2 hours | bright purple |
| 2.0% | 10 seconds | greenish yellow |
| 5.0% | 5 seconds | greenish yellow |

Comparative Example 4

This Example is included to illustrate the importance of balancing the parameters of the scheme used in the invention.

By using a similar system to that illustrated in Example 2 but increasing the concentration of sodium carbonate to produce a 0.1 M aqueous solution having a pH of 11.6 before addition of the hygroscopic liquid, the system behaves as follows:

| $CO_2$ Concentration | Contact Time | Color of Strip |
| --- | --- | --- |
| 0.03% | 3 hours | blue |
| 0.3% | 10 minutes | blue |
| 5.0% | 20 seconds | blue |
| 100% | 1 second | yellow |

Since the strip did not change color in less than 20 seconds in the presence of 5.0% carbon dioxide, it lacks the rapid response required and therefore is not suitable for a device according to the invention.

In contrast, a thymol blue system using a 0.00016 M aqueous solution of sodium carbonate having a pH of approximately 10.0 before addition of the hygroscopic liquid also is not suitable for a device according to the invention because, in this case, the contact time for a color change is the presence of 0.03% or 0.3% carbon dioxide is too short, accentuating the problem discussed in Example 2.

EXAMPLE 5

A 0.1 M aqueous solution of sodium hydroxide was prepared by dissolving sodium hydroxide in 5 ml of carbon dioxide-free distilled water. 0.005% w/v thymol blue was added followed by an equal volume of propylene glycol. The resultant solution was absorbed on Whatman No. 1 filter paper.

The impregnated paper strip was exposed to varying concentrations of carbon dioxide and performed as follows:

| $CO_2$ Concentration | Contact Time | Color of Strip |
| --- | --- | --- |
| 0.03% | 45 minutes | blue |
| 0.3% | 50 seconds | blue |
| 5.0% | 1 second | green |

Lithium hydroxide was substituted for sodium hydroxide with similar results.

EXAMPLE 6

An aqueous solution containing 0.6% monoethanolamine was prepared by dissolving the monoethanolamine in 5 ml. of carbon dioxide-free, distilled water. 0.005% w/v metacresol purple was added to the solution followed by an equal volume of propylene glycol.

The resultant mixture was absorbed on filter paper in a similar manner to that illustrated in previous Examples. Exposure to various concentrations of carbon dioxide gave the following results:

| $CO_2$ Concentration | Contact Time | Color of Strip |
| --- | --- | --- |
| 0% | ∞ | deep purple |
| 0.03% | 0.5 second | light purple |
| 0.03% | 1 hour | light purple |
| 0.3% | 3 minutes | light purple |
| 2.0% | 8 seconds | greenish yellow |
| 5.0% | ~1 second | yellow |

EXAMPLE 7

Example 6 was repeated using a 2.5% solution of monoethanolamine and thymol blue as indicator. The following results were obtained:

| $CO_2$ Concentration | Contact Time | Color of Strip |
| --- | --- | --- |
| 0% | ∞ | blue |
| 0.03% | 1 second | blue-green |
| 0.03% | 3 hours | blue-green |
| 2.0% | 8 seconds | green |
| 5.0% | 2 seconds | yellow-green |

Within one second of exposure to ambient air the surface pH drops from 12.4 to approximately 9.2 (blue-green color) but does not change thereafter to any measurable degree from this steady state value. However, exposure to 5% carbon dioxide rapidly causes a kinetic transition (yellow color) to occur, i.e. within one to two seconds.

BRIEF DESCRIPTION OF THE DRAWINGS

The preferred embodiment of the invention is a device for determining the placement of an endotracheal catheter in a patient and, consequently, the configuration of the device, particularly the enclosure, is such that it is adapted to be connected to a standard endotracheal catheter. The invention will now be particularly described with reference to such preferred embodiment as illustrated in the accompanying drawings in which:

FIG. 1 is an exploded view of the device showing the relative position of the component parts;

FIG. 2 is a side cross-section of the device fully assembled;

DETAILED DESCRIPTION OF THE DRAWINGS

Figure 3:
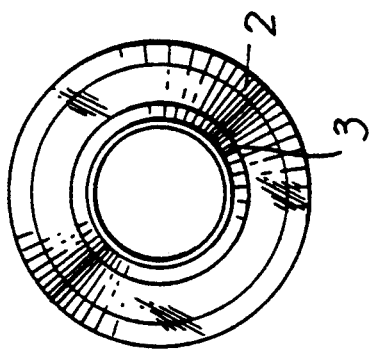
FIG. 3 is an end elevation of the inlet end of the device.

The preferred embodiment illustrated in FIGS. 1 and 2 of the drawings comprises a cylindrical housing 1 having at its proximal end a cone-shaped coupling 2 terminating in a cylindrical connector 3 and at its distal end a cone-shaped coupling 4 terminating in a cylindrical connector 5.

In this embodiment the proximal cone-shaped coupling 2 is integral with the cylindrical connector 3 and is made from a translucent white plastic, for example, polyethylene or polypropylene. The integral coupling/connector unit is separable from the housing 1 (FIG. 2) but is secured thereto by a screw thread 6.

Likewise, the distal cone-shaped coupling 4 is integral with the cylindrical connector 5, is made from a similar translucent plastic and is secured to the housing by a screw thread 7.

The cylindrical housing 1 is made from a clear, colorless, transparent plastic, for example, an acrylic polymer, such as that available under the Trademark PLEXIGLAS, polymethyl acrylate, polymethyl methacrylate, polycarbonate, polystyrene or styrene-acrylonitrile copolymer.

When the housing and coupling/connector units are connected to each other they effectively form an enclosure having an inlet formed by proximal connector 3 and an outlet formed by distal connector 5.

The clear transparent plastic used for the cylindrical housing provides an effective window 8 for viewing the indicator component 9, which comprises a strip of filter paper impregnated with an indicator element such as that illustrated in Example 1 herein. Fogging of said window by the humidity in exhaled breath is prevented by coating the inner surface of the window with a suitable anti-fogging surfactant, such as dioctyl sodium sulfosuccinate.

The indicator strip 9 is securely wrapped around the center of a cylindrical spool which is made from a rigid plastic, such as polyethylene. The spool 10 is mounted at each end on as inwardly facing flange 11 of a support 12.

Figure 4:
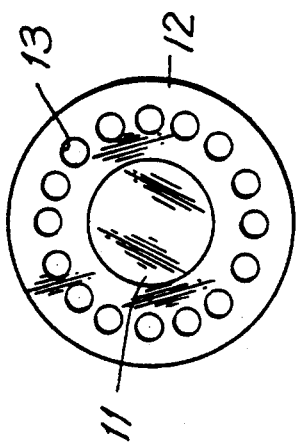
FIG. 4 is a plan of one of the spool supports.
Figure 5:
FIG. 5 is a side elevation of the support of FIG. 4.
Figure 4B:
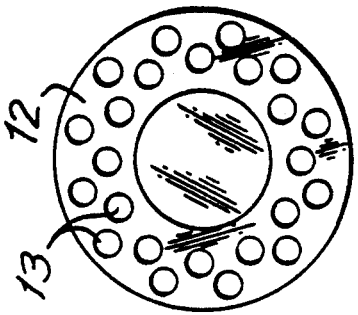
FIGS. 4a and 4b illustrate alternative configurations for the spool supports.
Figure 4A:
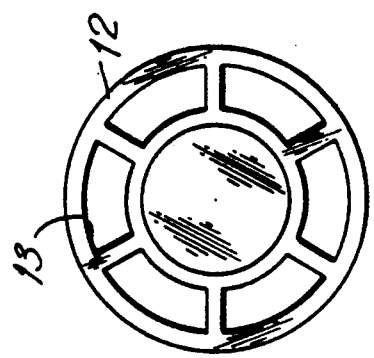

The supports 12 are substantially circular in shape and have a plurality of apertures 13 which allow substantially unrestricted flow of gas through the device when in use. Said apertures may be a series of circular holes, as illustrated in FIG. 4, or may be a different arrangement of holes as illustrated in FIGS. 4a and 4b.

The spool supports 12 are preferably made from a clear plastic, similar to that used for the cylindrical housing.

Each of the spool supports is mounted in a groove between each cone-shaped coupling and each end of the cylindrical housing, and is secured in place when each coupling is screwed to the housing, as illustrated in FIG. 2.

The device containing the indicating component mounted on the spool within the transparent cylindrical housing should be assembled under a carbon dioxide-free atmosphere and then sealed within a gas-impermeable metallic foil until required for use.

A device such as that described above having an indicator component as illustrated in Example 1 provides a rapid response and reliable means for visually detecting the presence of more than 2% carbon dioxide in exhaled breath passing through a catheter placed i the trachea of an apneic patient, in accordance with the method described herein.

I claim:

1. A method for determining whether a gaseous sample contains a predetermined concentration of carbon dioxide, comprising the step of:
   contacting the gaseous sample with a dry reagent detector comprising a carrier having an aqueous indicating composition applied thereto for providing an indication of the presence of the predetermined concentration of carbon dioxide in the sample within a diagnostically effective period of time when the carbon dioxide concentration in the sample is at least about 2% and providing said indication after about ten minutes when the carbon dioxide concentration in the sample is about 0.03%.

2. The method of claim 1 in which said carrier comprises an inert bibulous material.

3. The method of claim 1 in which said carrier comprises an inert fibrous material.

4. The method of claim 1 in which said carrier comprises an inert porous material.

5. The method of claim 1 in which said carrier comprises cellulose.

6. The method of claim 1 in which said diagnostically effective period of time is up to about twenty seconds.

7. The method of claim 6 in which said diagnostically effective period of time is from about two to about ten seconds.

8. The method of claim 1 in which said indication is visually observable.

9. The method of claim 1 in which said indicating composition consists essentially of a chromogenic material, a hygroscopic, water-miscible liquid and an aqueous alkaline solution.

10. The method of claim 9 in which said chromogenic material comprises a chromogenic ph indicator.

11. The method of claim 10 in which the aqueous alkaline solution is a solution of calcium hydroxide and the chromogenic pH indicator is selected from the group comprising metacresol purple and chromogenic pH indicators having pK values substantially the same as metacresol purple.

12. The method of claim 10 in which a predetermined relationship exists between the pH of said indicating composition and the pK of said chromogenic pH indicator.

13. The method of claim 12 in which said chromogenic pH indicator has a pK in said solution which is lower by about 0.5–2.8 pH units than the pH of said aqueous alkaline solution.

14. The method of claim 13 in which said chromogenic pH indicator has a pK which is lower by about 1.0–1.5 pH units than the pH of said aqueous alkaline solution.

15. The method of claim 1 in which said indicating composition comprises predetermined amounts of a base and a hygroscopic material.

16. The method of claim 15 in which the pH of said base is in the range of from about 9.0 to about 10.2.

17. The method of claim 1 in which said indicating composition comprises carbonic anhydrase.

18. A method for determining whether a gaseous sample contains a predetermined concentration of carbon dioxide, comprising contacting the gaseous sample with a detector comprising a carrier to which a dried non-volatile indicating element has been applied, said indicating element providing a first response within a diagnostically effective period of time when the carbon dioxide concentration in the sample is at least about 2% but not providing said first response for more than about ten minutes when the carbon dioxide concentration in the sample is on the order of 0.03%, and providing a second response within said diagnostically effective period of time when the ample is replaced with ambient air.

19. The method of claim 18, in which said first response consists of a first observable color change and said second response consists of a second observable color change.

20. The method of claim 18 in which the sample is collected from a patient and the diagnostically effective period of time is substantially the time for a single breath exhalation or inhalation.

21. A method of making a respiratory gas detector comprising the steps of:

selecting an aqueous alkaline solution;

combining the aqueous alkaline solution with a chromogenic pH-sensitive indicator to form a composition;

correlating the nature and concentration of the composition to the nature and concentration of the pH-sensitive indicator so that the composition produces a predetermined response within a first predetermined period of time to the exposure thereof to carbon dioxide at a concentration of at least about 2% and produces a response for a second predetermined period of time longer than said first predetermined period of time when the composition is exposed only to concentrations of carbon dioxide of no more than about 0.03%;

depositing the composition on a carrier and drying said carrier to form a dry reagent respiratory gas detector.

22. The method of claim 21 further comprising the step of combing the aqueous alkaline solution and chromogenic pH-sensitive indicator with a hygroscopic, water-miscible liquid.

23. The method of claim 21 in which the carrier is cellulose.

24. The method of claim 21 in which said first predetermined period of time is within the range of from less than 2 to about 20 seconds.

25. The method of claim 21 in which said second predetermined period of time is within a period exceeding 10 minutes.

* * * * *